United States Patent
Krishnaswamy et al.

(10) Patent No.: US 7,778,698 B1
(45) Date of Patent: Aug. 17, 2010

(54) METHOD AND SYSTEMS FOR IDENTIFYING A VECTOR FOR MONITORING ISCHEMIA

(75) Inventors: Harish Krishnaswamy, Mountain View, CA (US); Anil Keni, Bakersfield, CA (US)

(73) Assignee: Pacesetter, Inc., Sylmar, CA (US)

( * ) Notice: Subject to any disclaimer, the term of this patent is extended or adjusted under 35 U.S.C. 154(b) by 230 days.

(21) Appl. No.: 11/760,479

(22) Filed: Jun. 8, 2007

(51) Int. Cl.
A61B 5/04 (2006.01)

(52) U.S. Cl. ............... 600/509; 600/508; 600/512; 607/25

(58) Field of Classification Search ............ 607/25, 607/512, 24, 17, 9; 600/519, 517, 5, 508–512
See application file for complete search history.

(56) References Cited

U.S. PATENT DOCUMENTS

| 6,865,420 | B1 | 3/2005 | Kroll |
| 7,218,960 | B1 * | 5/2007 | Min et al. ............ 600/509 |
| 2002/0016548 | A1 * | 2/2002 | Stadler et al. ............ 600/509 |
| 2005/0209525 | A1 * | 9/2005 | Bojovic et al. ............ 600/512 |
| 2006/0116593 | A1 | 6/2006 | Zhang et al. |

FOREIGN PATENT DOCUMENTS

WO    WO2006/039693    4/2006

* cited by examiner

*Primary Examiner*—Carl H Layno
*Assistant Examiner*—Paula J Stice

(57) ABSTRACT

Methods and systems may identify a vector or a vector configuration, such as a combination of electrodes, for monitoring ischemia. The method may include: selecting a first combination of sensors as a first candidate to be used for monitoring ischemia; detecting a shift in a ST segment of one of an electrocardiogram and a cardiac electrogram using the first candidate; selecting a second combination of sensors as a second candidate to be used for monitoring ischemia; detecting a shift in a ST segment of one of an electrocardiogram and a cardiac electrogram using the second candidate; comparing the ST shifts for the first and second candidates; and identifying one of the first and second candidates for monitoring ischemia based on the comparison. A multi-electrode implantable cardiac device may include a controller configured to effectuate such functions.

16 Claims, 3 Drawing Sheets

METHOD AND SYSTEMS FOR IDENTIFYING A VECTOR FOR MONITORING ISCHEMIA

FIELD OF THE INVENTION

The present invention relates to medical devices and methods of using such devices. More specifically, the present invention relates to medical devices and methods for monitoring ischemia.

BACKGROUND OF THE INVENTION

Myocardial ischemia is a condition during which heart tissue is slowly or suddenly starved of oxygen and other nutrients due to a deficient supply of blood, for example, due to obstruction of the inflow of arterial blood. In particular, myocardial ischemia is an intermediate condition in coronary artery disease. The affected heart tissue will eventually die from prolonged ischemia. Further, when blood flow is completely blocked to the heart, ischemia may lead to a myocardial infarction or heart attack.

There is a need in the art for systems and methods for monitoring of myocardial ischemia.

SUMMARY

Various embodiments of the present invention take advantage of the multiple electrodes that are available for pacing and/or sensing in known implantable cardiac devices. It would be beneficial to be able to determine a preferred or optimal vector or vector configuration for monitoring myocardial ischemia, for example, to assess the existence, the exacerbation and/or the alleviation of myocardial ischemia in a patient.

Embodiments of the present invention contemplate using a plurality of vector configurations to provide a more comprehensive view of the myocardial ischemic condition. Not only may such embodiments provide an ability to monitor multiple vectors, but also identification, selection and/or suggestion of a particular vector or vector configuration for optimization of the vector configuration for monitoring may be enabled.

As such, some embodiments of the present invention may provide a system for identifying a vector for a preferred or optimal vector configuration for a multiple-sensor device including a plurality of vector configurations. Some embodiments of the present invention may provide a method of identifying a vector for a preferred or optimal vector configuration for a multiple-sensor device including a plurality of vector configurations.

Some embodiments of the present invention contemplate identifying, selecting and or suggesting a combination of electrodes corresponding to a preferred or optimal vector configuration. Specifically, some embodiments of the invention contemplate comparing outputs from a plurality of vector configurations to identify, select and suggest or use a particular combination of electrodes for monitoring myocardial ischemia. Such an approach may result in an improved or optimal vector configuration for monitoring myocardial ischemia.

The present invention, in one embodiment, is a method of identifying a vector for monitoring ischemia. The method may comprise: selecting a first combination of sensors as a first candidate to be used for monitoring ischemia; detecting a shift (e.g., a deviation or change) in a ST segment of one of an electrocardiogram and a cardiac electrogram using the first candidate; selecting a second combination of sensors as a second candidate to be used for monitoring ischemia; detecting a shift in a ST segment of one of an electrocardiogram and a cardiac electrogram using the second candidate; comparing the ST shifts for the first and second candidates; and identifying one of the first and second candidates for monitoring ischemia based on the comparison.

The present invention, in one embodiment, is a system for identifying a vector for monitoring ischemia. The system may comprise: means for selecting a plurality of combinations of sensors as candidates to be used for monitoring ischemia; means for detecting a shift (e.g., deviation or change) in a ST segment of one of an electrocardiogram and a cardiac electrogram using each of the candidates; means for comparing the ST shifts for each of the candidates; and means for identifying one of the candidates for monitoring ischemia based on the comparison.

The present invention, in one embodiment, is an implantable cardiac device for monitoring ischemia. The device may comprise: a plurality of electrodes configured to be used for sensing; a pulse generator in electrical communication with the plurality of electrodes; and a controller configured to select a plurality of candidates for monitoring ischemia, each of the candidates consisting of a combination of the plurality of electrodes, to receive a shift (e.g., deviation or change) in a ST segment of one of an electrocardiogram and a cardiac electrogram detected using each of the candidates, and to identify one of the candidates for monitoring ischemia based on a comparison of the detected ST shifts.

The present invention, in one embodiment, is a method of monitoring ischemia in a patient. The method may comprising: for each electrode vector configuration of a plurality of electrode vector configurations, determine a shift (e.g., deviation or change) of a ST segment of an electrocardiogram and/or a cardiac electrogram; identify from the plurality of electrode vector configurations a first electrode vector configuration having the most magnified shift of a ST segment; and select the first electrode vector configuration as window for monitoring ischemia in the patient.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

The following description is of embodiments presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Embodiments of the present invention are described in relation to a cardiac stimulation device capable of delivering precisely ordered stimulation pulses to multiple chambers of the heart, referred to herein as multi-chamber stimulation, or to multiple sites within a chamber of the heart, referred to herein as multi-site stimulation. As used herein, the shape of the stimulation pulses is not limited to an exact square or rectangular shape, but may assume any one of a plurality of shapes, which is adequate for the delivery of an energy packet or stimulus.

The stimulation device is intended for use in patients suffering from hemodynamic dysfunction, which may or may not be accompanied by conduction disorders. Precisely controlled stimulation at multiple sites or in multiple chambers is provided to intentionally make use of the pacing function of the heart to improve cardiac hemodynamics by re-coordinating heart chamber contractions and/or preventing arrhythmogenic depolarizations from occurring. Thus, the cardiac stimulation device is capable of delivering at least low-voltage stimulation pulses to multiple stimulation sites for providing pacing therapy, and may include high-voltage stimulation shocks for providing cardioversion therapy and defibrillation therapy.

The disclosed device and method are directed at monitoring myocardial ischemia. Such monitoring may occur, for example, during cardiac stimulation using an implantable cardiac device, such as a defibrillator or a pacemaker. Thus, the methods described herein may be incorporated in any such cardiac stimulation device. A general cardiac stimulation device will thus be described in conjunction with FIGS. 1 and 2, in which the myocardial ischemia detection methods described herein may be implemented. It should be understood, however, that numerous variations exist of such a device in which the methods may be implemented.

Figure 1:
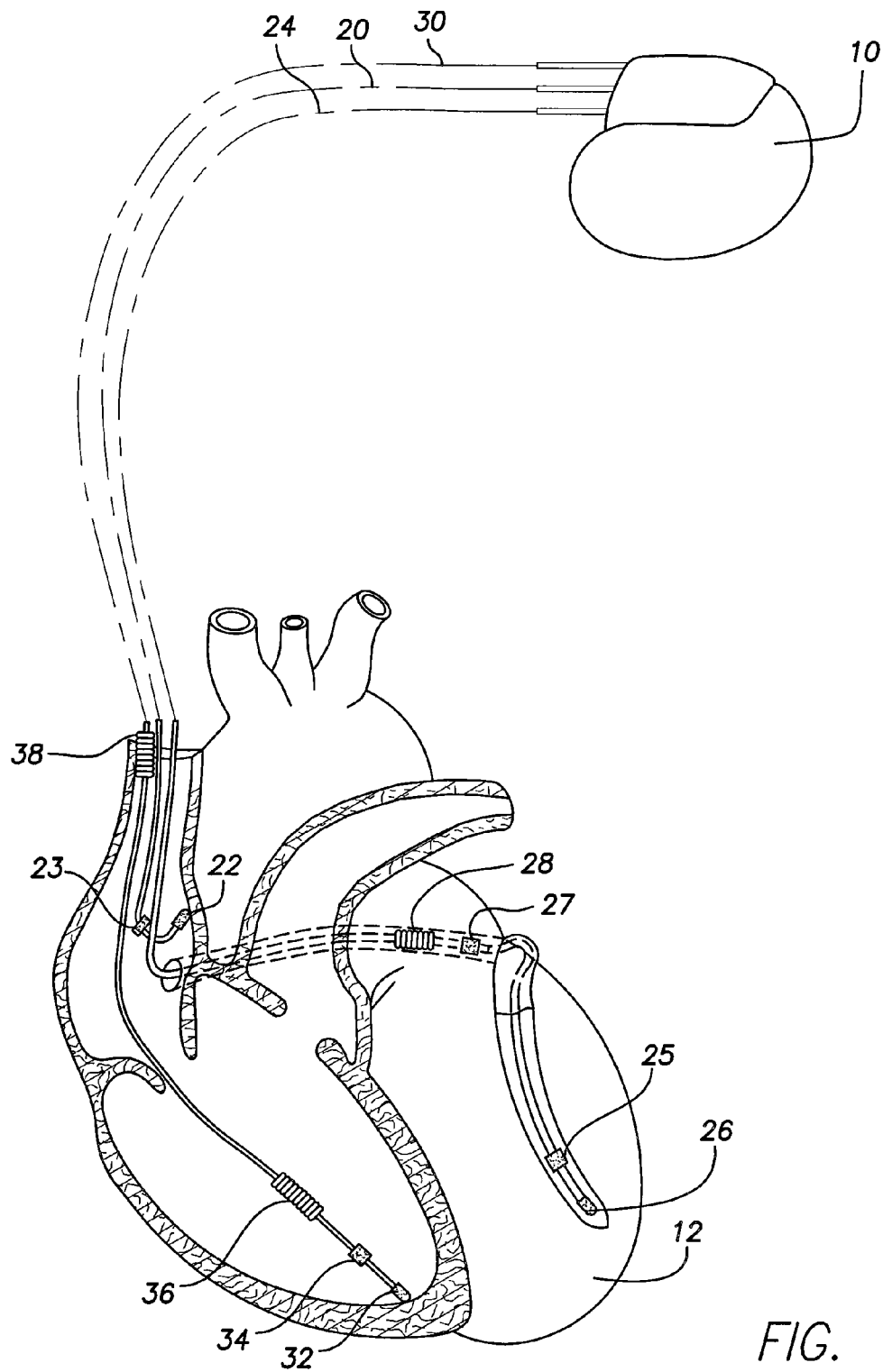
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 via three leads 20, 24 and 30, for example, suitable for delivering multi-chamber stimulation and/or shock therapy. To sense atrial cardiac signals and to provide right atrial chamber stimulation therapy, the stimulation device 10 may be coupled to an implantable right atrial lead 20 including at least an atrial tip electrode 22, which typically is implanted in the patient's right atrial appendage. The right atrial lead 20 may also include an atrial ring electrode 23 to allow bipolar stimulation or sensing in combination with the atrial tip electrode 22.

To sense the left atrial and ventricular cardiac signals and to provide left-chamber stimulation therapy, the stimulation device 10 may be coupled to a "coronary sinus" lead 24 designed to be placed in the "coronary sinus region" via the coronary sinus ostium so as to place at least a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 may be designed to: receive atrial and ventricular cardiac signals; deliver left ventricular pacing therapy using at least a left ventricular tip electrode 26 for unipolar configurations or in combination with left ventricular ring electrode 25 for bipolar configurations; deliver left atrial pacing therapy using at least a left atrial ring electrode 27, and deliver shocking therapy using at least a left atrial coil electrode 28.

The stimulation device 10 is also shown in electrical communication with the patient's heart 12 via an implantable right ventricular lead 30 including, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 may be capable of receiving cardiac signals and delivering stimulation in the form of pacing and/or shock therapy to the right ventricle.

Figure 2:
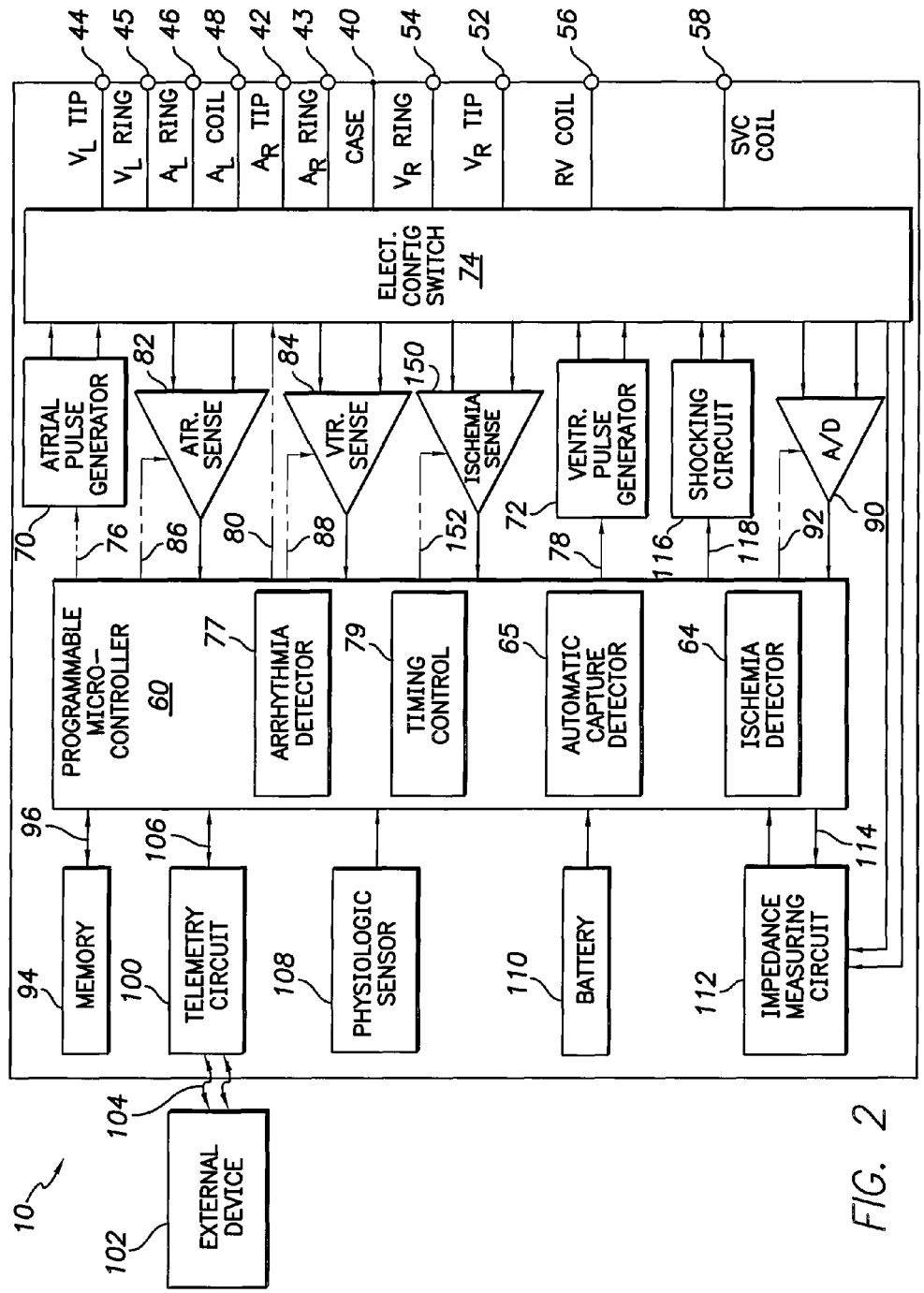
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which may be capable of treating both fast and slow arrhythmias with stimulation therapy, including cardioversion, defibrillation, and/or pacing stimulation. The stimulation device 10 may also be capable of automatically adjusting stimulation parameters to provide an optimized cardiac output according to a patient's activity level or metabolic demand and/or for the treatment of congestive heart failure. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 may include a housing 40, which is often referred to as a "can", a "case" or a "case electrode", and which may be programmably selected to act as a return electrode for all "unipolar" modes. The housing 40 may further be used as a return electrode alone or in combination with one or more of the coil electrodes 28, 36, or 38, for example, for defibrillation shocking purposes. In accordance with one embodiment, the housing 40 may be used as the return electrode during sensing of intracardiac electrogram (EGM) signals for the detection of myocardial ischemia.

The housing 40 may further include a connector with a plurality of terminals 42, 43, 44, 45, 46, 48, 52, 54, 56, and 58 (shown schematically and, for convenience, the names of the electrodes to which they are connected are shown next to the corresponding terminals). As such, to achieve right atrial sensing and/or stimulation, the connector may include at least a right atrial tip terminal ($A_R$ TIP) 42 adapted for connection to the atrial tip electrode 22. The connector may also include a right atrial ring terminal ($A_R$ RING) 43 for connection to the right atrial ring electrode 23.

To achieve left chamber sensing, pacing, and/or shocking, the connector may include at least a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, which are adapted for connection to the left ventricular tip electrode 26, the left ventricular ring electrode 25, the left atrial ring electrode 27, and the left atrial coil electrode 28, respectively.

To support right ventricular sensing, pacing and/or shocking, the connector further may include a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 may be a programmable microcontroller 60 that is configured to control the various modes of sensing and/or stimulation therapy. The microcontroller 60 may include a microprocessor, or equivalent control circuitry, designed specifically for controlling the sensing or delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

FIG. 2 illustrates an atrial pulse generator 70 and a ventricular pulse generator 72 that are configured to respectively generate stimulation pulses for delivery by the right atrial lead 20, the right ventricular lead 30, and/or the coronary sinus lead 24 via a switch 74. It should be understood that to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 may be controlled by the microcontroller 60 via appropriate control signals 76 and 78, respectively, to trigger or inhibit the stimulation pulses.

The microcontroller 60 may further include timing control circuitry 79, which may be configured to control the timing of such stimulation pulses (e.g., pacing rate, atrio-ventricular (AV) delay, atrial interchamber (A—A) delay, or ventricular interchamber (V—V) delay, etc.), as well as to keep track of the timing of refractory periods, noise detection windows, evoked response windows, alert intervals, marker channel timing, etc.

The switch 74 may include a plurality of switches for connecting the desired electrodes to the appropriate I/O circuits, thereby providing complete electrode programmability. Accordingly, the switch 74, in response to a control signal 80 from the microcontroller 60, may determine the polarity of the stimulation pulses (e.g., unipolar, bipolar, cross-chamber, etc.) by selectively closing the appropriate combination of switches.

Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 may determine the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 may employ one or more low power, precision amplifiers with programmable gain and automatic gain or sensitivity control, bandpass filtering, and a threshold detection circuit, to selectively sense a cardiac signal of interest. The automatic sensitivity control may enable the stimulation device 10 to deal effectively with the difficult problem of sensing the low amplitude signal characteristics of atrial or ventricular fibrillation.

The outputs of the atrial and ventricular sensing circuits 82 and 84 may be connected to the microcontroller 60 for triggering or inhibiting the atrial and ventricular pulse generators 70 and 72, respectively, in a demand fashion, in response to the absence or presence of cardiac activity, respectively, in the appropriate chambers of the heart (i.e., pacing and/or defibrillation). The atrial and ventricular sensing circuits 82 and 84, in turn, may receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

In one embodiment, stimulation device 10 may further include an ischemia sensing circuit 150 dedicated to sensing EGM signals that are evaluated for changes indicative of myocardial ischemia by an ischemia detector 64, for example, included in the microcontroller 60. As will be understood with respect to FIG. 3, desired combinations of electrodes may be connected to ischemia sensing circuit 150 through switch 74, for example, to test various combinations for monitoring ischemia.

The output of ischemia sensing circuit 150 may be connected to the microcontroller 60. The ST-segment of sensed EGM signals may be analyzed by ischemia detector 64 to detect changes in the ST-segment or T-wave amplitude that correspond to myocardial ischemia. Although not described in detail below, and not shown in FIGS. 1 and 2, it should be understood that electrocardiogram (ECG) signals may also be sensed using surface electrodes (e.g., epicardial electrodes) connected to the heart 12. As such, such surface electrodes may be included in the possible combinations for monitoring ischemia. For the sake of clarity and simplicity, however, only the intracardial electrodes illustrated in FIGS. 1 and 2 are described below.

For arrhythmia detection, the stimulation device 10 may include an arrhythmia detector 77 that utilizes the atrial and ventricular sensing circuits 82 and 84 to sense cardiac signals, for determining whether a rhythm is physiologic or pathologic. Arrhythmia detection may be performed as is known in the art.

Cardiac signals may be applied to the inputs of a data acquisition system 90, which is depicted as an analog-to-digital (A/D) converter for simplicity of illustration. The data acquisition system 90 may be configured to acquire EGM signals (and/or ECG signals as noted above), convert the raw analog data into digital signals, and store the digital signals for later processing and/or telemetric transmission to an external device 102. The data acquisition system 90 may be coupled to the right atrial lead 20, the coronary sinus lead 24, and the right ventricular lead 30 through the switch 74 to sample cardiac signals across any pair of desired electrodes. In one embodiment, data acquisition system 90 may be used to acquire EGM signals for the analysis of changes in the ST-segment for detecting myocardial ischemia.

Advantageously, the data acquisition system 90 may be coupled to the microcontroller 60 or another detection circuitry, for detecting an evoked response from the heart 12 in response to an applied stimulus, thereby aiding in the detection of "capture". In the embodiment shown in FIG. 2, the microcontroller 60 may include an automatic capture detector 65 that searches for an evoked response signal following a stimulation pulse during a "detection window" set by timing control circuitry 79.

The microcontroller 60 may enable the data acquisition system 90 via control signal 92 to sample the cardiac signal that falls in the capture detection window. The sampled signal may be evaluated by an automatic capture detector 65 to determine if it is an evoked response signal based on its amplitude, peak slope, morphology or another signal feature or combination of features. The detection of an evoked response during the detection window indicates that capture has occurred.

The microcontroller 60 may further be coupled to a memory 94 by a suitable data/address bus 96, wherein the programmable operating parameters used by the microcontroller 60 are stored and modified, as required, to customize the operation of the stimulation device 10 to suit the needs of a particular patient. Such operating parameters may define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy. Further, such operating parameters may define ischemia detection criteria and/or vector configurations for monitoring ischemia.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 may be activated by the microcontroller 60 by a control signal 106. The telemetry circuit 100 advantageously may allow intracardiac electrograms and status information relating to the operation of the stimulation device 10 (as contained in the microcontroller 60 or memory 94) to be sent to the external device 102 through an established communication link 104.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states), which may be used to adjust the various stimulation parameters, for example.

The stimulation device 10 may additionally include a power source such as a battery 110 that provides operating power to all the circuits shown in FIG. 2. As further illustrated in FIG. 2, the stimulation device 10 may include an impedance measuring circuit 112, which may be enabled by the microcontroller 60 by control signal 114. Known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 advantageously may be coupled to the switch 74 so that any desired electrode may be used.

If it is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 may further control a shocking circuit 116 via a control signal 118. The shock therapy may be applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV coil electrode 36, or as part of a split electrical vector using the SVC coil electrode 38 or the left atrial coil electrode 28.

The electrode configuration switch 74 illustrated in FIG. 2 may allow various electrode combinations to be used to monitor ischemia. For example, the electrode configuration switch 74 may advantageously provide all possible electrode combinations for monitoring ischemia. However, for the methods, systems and devices contemplated by the present invention, only a plurality (at least two) of electrode combinations may be provided. As discussed herein, each different electrode combination provides a different vector that may be used for monitoring ischemia. Thus, a particular electrode combination may be identified as a preferred or optimal vector among plural vectors for monitoring ischemia.

In one embodiment, the goal may be to identify, select and/or use one of the combinations of electrodes for monitoring ischemia. It should be understood that more than one combination of electrodes may be identified for monitoring ischemia. However, for the sake of clarity and simplicity, the description herein is in terms of identifying one combination of electrodes.

In some embodiments, results for all vectors or combinations of electrodes may be provided to a user to give a comprehensive view of ischemia. Thus, the user may use such information to determine whether to employ a suggested parameter for monitoring ischemia (e.g., a preferred or optimal vector configuration) or to set their own.

Such an approach may selectively test individual candidates comprising a combination of electrodes to determine a shift in a ST segment of a cardiac electrogram (EGM) for each of a plurality of candidates. The ST shifts may be compared and one of the candidates may be identified for monitoring ischemia based on the comparison. In particular, the candidate may be identified as the one with a largest ST deviation, i.e., the largest deviation in the ST segment.

Figure 3:
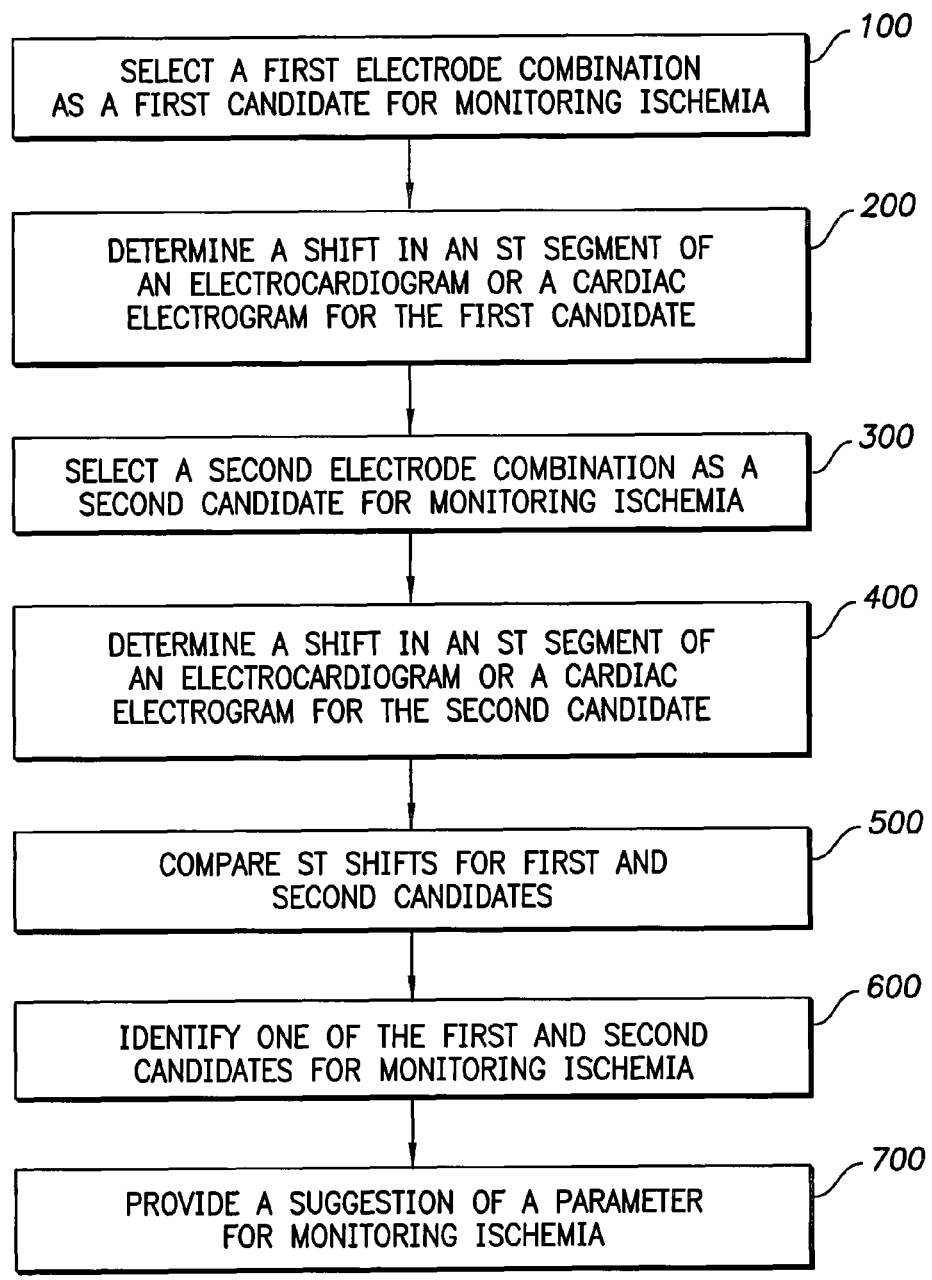
FIG. 3 is simplified block diagram illustrating a process for identifying a vector configuration for monitoring ischemia.

For example, as outlined in FIG. 3, a first vector may be defined by a first vector configuration that employs the case or housing 40 and the $R_V$ TIP electrode ($R_V$ TIP to case vector). A second vector may be defined by a second vector configuration that employs the $L_V$ RING electrode and the $R_V$ RING electrode ($L_V$ RING to $R_V$ RING vector). The first and second vectors may be selected as candidates for monitoring ischemia [BLOCKS 100 AND 300] (although any number of candidates may be selected as desired). For each candidate, a shift in a ST segment of a cardiac electrogram or electrocardiogram may be detected or otherwise determined [BLOCKS 200 AND 400].

To detect the ST shifts, an electrical pulse may be sent to each of the electrode combinations, for example, via the appropriate atrial pulse generator 70 or ventricular pulse generator 72. The electrical pulse will cause responses in the heart tissue that may be sensed by the respective electrode combination as a signal including a ST segment. The shift in the ST segment of each signal may then be compared [BLOCK 500]. Based on the comparison, one of the candidates may be identified for monitoring ischemia [BLOCK 600], for example, as a preferred or optimal vector for monitoring ischemia.

The preceding discussion describes an active approach, wherein the pulse generators send an electrical pulse, which causes responses in the heart tissue that may be sensed by an electrode combination as a signal including a ST segment. However, a passive approach can function in a similar way. Specifically, an intrinsic pulse (i.e., a pulse generated by the heart itself) is awaited, and the intrinsic pulse causes responses in the heart tissue that may be sensed by an electrode combination as a signal including a ST segment.

In some embodiments, the approach may include providing a suggestion of a parameter for monitoring ischemia [BLOCK 700]. Such a parameter may be a particular vector configuration to use.

A deviation or shift in a ST segment can be measured or otherwise quantified via a number of methods. For example, the ST deviation or shift can be quantified as a voltage shift in a ST segment. In other embodiments, the ST deviation or shift can be quantified as a percentage of the R peak, as binary counts, millimeters, etc.

The various possible vector configurations may provide different "views" of myocardial ischemia or "windows" for viewing myocardial ischemia. The amount of ischemic activity observed via a particular vector configuration may be highly dependent on the particular vector utilized as the window for viewing myocardial ischemia. In particular, deviation in the ST segment may be substantially different from one vector to another. For example, one vector configuration may provide a ST deviation that is detectable, whereas another vector configuration may not provide any detectable ST deviation. Thus, each vector configuration may provide a different view or indication of myocardial ischemia.

By comparing the ST deviation for a plurality of vector configurations, a preferred or optimal vector or vector configuration may be identified for monitoring ischemia. Thus, embodiments of the present invention may effectively manage multiple vector configurations for monitoring ischemia and identify a preferred or optimal vector configuration. In particular, a user may be able to initiate such an approach and allow the vector configuration to be optimized for monitoring ischemia automatically. Once the evaluation process is completed for the possible or selected vector configurations, the user may be provided with a suggestion, as discussed above, or the identified vector configuration may be automatically implemented without further user input.

Further, by obtaining signals from multiple vector configurations, a more comprehensive view of ischemic activity in the heart may be provided to a user. Such a comprehensive view may enhance the user's ability to determine various parameters for monitoring ischemia.

In general, the various components illustrated in FIGS. 1 and 2 may be used to carry out a process of identifying a preferred or optimum vector configuration as illustrated in FIG. 3. It should be understood, however, that other configurations of the implantable stimulation device 10 may be employed to carry out such a process.

Further, although not shown for the sake of simplicity, it should be understood that suitable loops may be included in the illustrative process of FIG. 3 to process three or more candidates. Such a loop may occur before or after a comparison is made, as appropriate or desired.

The foregoing description is set forth in terms that are adaptable to a user initiated process or a fully automated process. As such, it is also contemplated that the foregoing may be used to provide ongoing reconfiguration for optimal monitoring of ischemia. For example, the memory 94 of the implantable cardiac device 10 may include a program that causes the microcontroller 60 to periodically evaluate the vector configurations. Thus, not only may a physician optimally configure the device 10 for monitoring ischemia, for example, upon implantation, the physician may allow the device 10 to self-adjust based on on-going data, without further physician action or with minimal physician involvement.

Providing an optimal configuration for monitoring ischemia may simplify the monitoring process, for example by reducing the number of vector configurations actually used to monitor ischemia. Absent the identification of a preferred or optimal vector configuration for monitoring ischemia, it may be necessary to simultaneously employ a large number of vector configurations to provide reliable monitoring, for example, to allow for vector configurations that fail to provide sufficient indications of ischemic activity.

Also, by providing an optimal configuration for monitoring ischemia, improved data regarding ischemic activity in the heart may be obtained. The improved data may more fully characterize ischemic activity, and thus allow the systems and methods designed to respond to ischemic activity, whether presently known or hereafter developed, to respond effectively.

Typically, no one particular lead vector can illustrate the whole story of ischemic activity in the heart. In one embodiment of the above-described invention, a user will initiate an ischemia detection algorithm that will automatically gather ST shifts on multiple lead vector configurations (e.g., $R_V$TIP to case vector, $L_V$TIP to case vector, $L_V$RING to $R_V$RING vector, etc.). The multiple lead vector configurations employed could be at least two different lead vector configurations, all possible lead vector configurations, or any number of lead vector configurations there between.

The algorithm provides to the user (e.g., via a display) the ST voltage trends per lead vector configuration with a suggestion on how to best program the lead vector configuration. The user will then have the opportunity to either accept the suggested programming parameters or manually change the vector configuration to suit his/her desire. The algorithm will then use this specific "window" used to view ischemic activity in the heart until the algorithm is re-optimized. In one embodiment, the specific "window" used to view the ischemic activity will be the electrode vector configuration having the most magnified deviation on the ST shift.

Ultimately, in one embodiment of the above-described invention, the algorithm optimizes the viewing or monitoring of ischemic activity by comparing multiple "windows" (i.e., electrode vector configurations) to determine which "window" provides the best mechanism for viewing or monitoring ischemic activity. In one embodiment, the best mechanism for viewing or monitoring the ischemic activity will be the electrode vector configuration having the most magnified deviation on the ST shift.

In one embodiment of the above-described invention, the algorithm determines the ST shift for two or more of the possible electrode vector configurations. In one embodiment of the above-described invention, the algorithm determines the ST shift for all or substantially all of the possible electrode vector configurations. Regardless of the number of electrode vector configurations for which ST shift determinations are made, the ST shift determinations are compared to each other to determine which ST shift has the greatest magnified deviation. The electrode vector configuration associated with the ST shift having the greatest magnified deviation can then be selected (automatically or by the user) to monitor or view ischemia conditions, thereby providing a high level view of ischemia in the patient.

In one embodiment of the above-described invention, two or more electrodes (e.g., electrodes 22 and 23) on a lead (e.g., the coronary sinus lead 20) can be electronically coupled together to operate as a single, larger sensing surface (e.g., a single, larger coronary sinus lead sensing surface). Two or more electrodes (e.g., electrodes 32 and 34) on another lead (e.g., the right ventricular lead 30) can be electronically coupled together as a single, larger sensing surface (e.g., a single, larger right ventricular lead sensing surface). The algorithm can then create electrode vector configurations between: the single, larger coronary sinus lead sensing surface and the single, larger right ventricular lead sensing surface; the single, larger coronary sinus lead sensing surface and the case of the pulse generator; and the single, larger right ventricular lead sensing surface and the case of the pulse generator. The algorithm can then determine which electrode vector configuration provides the ST shift with the greatest magnified deviation. This electrode configuration can then be automatically selected or selected by the user as a "window" for high level viewing ischemia in the patient.

Although the present invention has been described with reference to preferred embodiments, persons skilled in the art will recognize that changes may be made in form and detail without departing from the spirit and scope of the invention.

What is claimed is:

1. A method of identifying a vector for monitoring ischemia, the method comprising:
   selecting a first combination of sensors as a first candidate to be used for monitoring ischemia;
   detecting a shift in a ST segment of one of an electrocardiogram and a cardiac electrogram using the first candidate;
   selecting a second combination of sensors as a second candidate to be used for monitoring ischemia;
   detecting a shift in a ST segment of one of an electrocardiogram and a cardiac electrogram using the second candidate;
   comparing the ST shift of the first candidate to the ST shift of the second candidate; and
   identifying one of the first and second candidates for monitoring ischemia based on the comparison.

2. The method of claim 1, wherein identifying one of the first and second candidates for monitoring ischemia based on the comparison comprises identifying the candidate with a largest ST deviation.

3. The method of claim 1, wherein the first and second combinations of sensors comprise electrodes.

4. The method of claim 1, wherein at least detecting the ST shifts is accomplished using an implantable cardiac electrotherapy device.

5. The method of claim 1, further comprising providing a result to a user for each detection.

6. The method of claim 1, further comprising providing a suggestion of a parameter for monitoring ischemia based on the comparison.

7. The method of claim 6, wherein the parameter comprises a vector configuration.

8. The method of claim 1, further comprising selecting the identified candidate for monitoring ischemia.

9. A system for identifying a vector for monitoring ischemia, the system comprising:
   means for selecting a plurality of combinations of sensors as candidates to be used for monitoring ischemia;
   means for detecting a shift in a ST segment of one of an electrocardiogram and a cardiac electrogram using each of the candidates;
   means for comparing the ST shifts for each of the candidates to one another; and
   means for identifying one of the candidates for monitoring ischemia based on the comparison.

10. The system of claim 9, wherein the means for identifying one of the candidates for monitoring ischemia based on the comparison is configured to identify the candidate with a largest ST deviation.

11. The system of claim 9, wherein each of the plurality of combinations of sensors comprises a combination of electrodes.

12. The system of claim 9, wherein the means for detecting the ST shifts comprises an implantable cardiac electrotherapy device.

13. The system of claim 9, further comprising means for providing a result to a user for each detection.

14. The system of claim 9, further comprising means for providing a suggestion of a parameter for monitoring ischemia based on the comparison.

15. The system of claim 14, wherein the parameter comprises a vector configuration.

16. The system of claim 9, further comprising means for selecting the identified candidate for monitoring ischemia.

* * * * *